(12) United States Patent
Cannaliato et al.

(10) Patent No.: US 10,102,261 B2
(45) Date of Patent: *Oct. 16, 2018

(54) SYSTEM AND METHOD FOR CORRELATING CLOUD-BASED BIG DATA IN REAL-TIME FOR INTELLIGENT ANALYTICS AND MULTIPLE END USES

(71) Applicant: Leidos, Inc., Reston, VA (US)

(72) Inventors: Thomas James Cannaliato, Sykesville, MD (US); Joshua A. Decker, Severna Park, MD (US); Matthew William Vahlberg, Severna Park, MD (US)

(73) Assignee: Leidos, Inc., Reston, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/900,329

(22) Filed: Feb. 20, 2018

(65) Prior Publication Data

US 2018/0173777 A1   Jun. 21, 2018

Related U.S. Application Data

(63) Continuation of application No. 15/356,918, filed on Nov. 21, 2016, now Pat. No. 9,922,107, which is a continuation of application No. 14/809,393, filed on Jul. 27, 2015, now Pat. No. 9,501,535, which is a (Continued)

(51) Int. Cl.
*G06F 17/30* (2006.01)
*G16H 10/60* (2018.01)
*G06F 21/62* (2013.01)
*G06F 19/00* (2018.01)

(52) U.S. Cl.
CPC .... *G06F 17/30569* (2013.01); *G06F 17/3048* (2013.01); *G06F 17/30294* (2013.01); *G06F 17/30303* (2013.01); *G06F 17/30377* (2013.01); *G06F 17/30424* (2013.01); *G06F 17/30539* (2013.01); *G06F 17/30592* (2013.01); *G06F 17/30595* (2013.01); *G06F 19/00* (2013.01);

(Continued)

(58) Field of Classification Search
USPC ................................................. 707/756, 799
See application file for complete search history.

(56) References Cited

U.S. PATENT DOCUMENTS 6,327,418 B1 * 12/2001 Barton ............... H04N 21/4331
    348/E5.007
6,850,999 B1   2/2005 Mak et al. ...................... 710/39

(Continued)

OTHER PUBLICATIONS

Kimball Group, "A Dimensional Modeling Manifesto," Aug. 2, 1997 [retrieved on May 8, 2013], Retrieved from the Internet: http://www.kimballgroup.com/1997/08/02a-dimensional-modeling-manifesto/.

*Primary Examiner* — Cam Linh T Nguyen
(74) *Attorney, Agent, or Firm* — Dawn-Marie Bey; Bey & Cotropia PLLC

(57) ABSTRACT

A processing platform integrates ETL (extract, transform, and load), real time stream processing, and "big data" data stores into a high performance analytic system that runs in a public or private cloud. The platform performs real time pre-storage enrichment of data records to form a single comprehensive record usable for analytics, searching and alerting. The platform further supports sharing of components and plug-ins and performs automatic scaling of resources based on real time resource monitoring and analysis.

21 Claims, 6 Drawing Sheets

Related U.S. Application Data continuation of application No. 13/776,112, filed on Feb. 25, 2013, now Pat. No. 9,092,502.

(52) U.S. Cl.
CPC ......... *G06F 21/6254* (2013.01); *G16H 10/60* (2018.01)

(56) References Cited

U.S. PATENT DOCUMENTS

| | | | | |
|---|---|---|---|---|
| 6,862,278 | B1* | 3/2005 | Chang | H04N 19/176 |
| | | | | 348/384.1 |
| 7,010,370 | B1* | 3/2006 | Riegelsberger | G10L 19/00 |
| | | | | 381/63 |
| 7,065,050 | B1 | 6/2006 | Herbst | 370/235 |
| 8,565,250 | B2 | 10/2013 | Nemawarkar et al. | 370/412 |
| 8,571,049 | B2 | 10/2013 | Pacella et al. | 370/412 |
| 2002/0183950 | A1 | 12/2002 | Fu et al. | 702/84 |
| 2003/0189935 | A1 | 10/2003 | Warden et al. | 370/395.21 |
| 2005/0066082 | A1 | 3/2005 | Forin et al. | 710/52 |
| 2005/0169291 | A1 | 8/2005 | Key et al. | 370/412 |
| 2005/0235164 | A1 | 10/2005 | Gassoway | 713/193 |
| 2007/0180119 | A1* | 8/2007 | Khivesara | H04L 12/1881 |
| | | | | 709/226 |
| 2007/0280111 | A1 | 12/2007 | Lund | 370/235 |
| 2008/0140387 | A1 | 6/2008 | Linker | 704/9 |
| 2008/0304516 | A1* | 12/2008 | Feng | G06F 9/5038 |
| | | | | 370/468 |
| 2009/0079960 | A1* | 3/2009 | Chung | G01S 17/023 |
| | | | | 356/28 |
| 2010/0031108 | A1* | 2/2010 | Peeters | H04L 1/1887 |
| | | | | 714/748 |
| 2010/0094829 | A1 | 4/2010 | Castellanos et al. | 707/705 |
| 2010/0138511 | A1* | 6/2010 | Guo | H04L 47/10 |
| | | | | 709/207 |
| 2010/0142376 | A1* | 6/2010 | Lou | H04L 47/10 |
| | | | | 370/236 |
| 2011/0087915 | A1* | 4/2011 | Zhang | H04L 12/1854 |
| | | | | 714/2 |
| 2011/0122883 | A1 | 5/2011 | Pacella et al. | 370/412 |
| 2012/0023498 | A1 | 1/2012 | Sundararaman et al. | 718/102 |
| 2013/0046826 | A1* | 2/2013 | Stanton | G06Q 10/10 |
| | | | | 709/204 |
| 2013/0067160 | A1* | 3/2013 | Ostrovsky | G06F 12/02 |
| | | | | 711/114 |
| 2013/0110854 | A1 | 5/2013 | Lockhart et al. | 707/756 |

\* cited by examiner

Figure 1 – Prior Art

SYSTEM AND METHOD FOR CORRELATING CLOUD-BASED BIG DATA IN REAL-TIME FOR INTELLIGENT ANALYTICS AND MULTIPLE END USES

CROSS-REFERENCE TO RELATED APPLICATIONS

The present application is a continuation of U.S. patent application Ser. No. 15/356,918, filed Nov. 1, 2016, titled "System and Method For Correlating Cloud-Based Big Data in Real-Time For Intelligent Analytics and Multiple End Uses," which is a continuation of U.S. patent application Ser. No. 14/809,393, filed Jul. 27, 2015, titled "System and Method For Correlating Cloud-Based Big Data in Real-Time For Intelligent Analytics and Multiple End Uses," now U.S. Pat. No. 9,501,535, which is a continuation of U.S. patent application Ser. No. 13/776,112, filed Feb. 25, 2013, titled "System and Method For Correlating Cloud-Based Big Data in Real-Time For Intelligent Analytics and Multiple End Uses" now U.S. Pat. No. 9,092,502, all of which are incorporated herein by reference in their entirety.

FIELD OF THE EMBODIMENTS

The embodiments relate in general to system and methods for correlating volumes of disparate data and enriching in real-time. More particularly, the embodiments are directed to a system and process for enriching incoming big data within the cloud to add dimensional data in order to enable post-cloud relating and use by different applications.

BACKGROUND OF THE EMBODIMENTS

The problem to be solved generally, is how to manage and analyze big data, e.g., on the order of petabytes of data. Big data is broadly defined as data sets with sizes beyond the ability of commonly-used software tools to capture, curate, manage, and process the data within a reasonable amount of time. The world's information doubles approximately every two years. This information (or data) includes critical intelligence, but the mining of such intelligence becomes cost prohibitive and takes too long for many end-users and applications. Whereas traditional data sets include narrow subsets of historical, structured, static data populating relational databases; big data presents a particularly difficult problem for end-users as it is unlimited, may be both structured and unstructured, is frequently available in real-time and may be iterative. Such big data is simply too much for the present relational database management systems without significant processing, which is time consuming and ultimately renders much of the data outdated and of limited value.

FIG. 1 illustrates an existing process for correlating data. As shown, multiple exemplary data sets $D_1$ to $D_4$ from various sources are loaded onto separate databases ($DB_1$ to $DB_4$) for separate access by an application or user (hereafter "user"). Additional contextual data to augment the relevance of sources $D_1$ through $D_4$ are accessible directly to the user ($D_5$ and $D_6$). The user must correlate and process the data from the data sets to generate a result. The report generation process is time consuming and highly manual, requiring a large investment of time from the user.

A number of existing data warehousing techniques address the backend correlation changes of scenarios such as depicted in FIG. 1 Dimensional modeling has been used to organize data in a data warehouse to increase its analytical value and support end-user queries by adding dimension data to fact data to provide context. This is described in multiple papers by Ralph Kimball; see, for example, "A Dimensional Modeling Manifesto" Aug. 2, 1997, Kimball Group (www.kimballgroup.com), which is incorporate herein by reference in its entirety. While the dimensional modeling technique is available to structure the data after it is saved in $DB_1$ to $DB_4$ to support end user queries, this is a backend technique.

Accordingly, there is a need in the art for an improved system and method for front end processing of big data for near real-time availability for alerting, query and analysis by one or more users.

SUMMARY OF THE EMBODIMENTS

In a first exemplary embodiment, a process for data collection and conditioning is described. The process includes: receiving multiple data records from multiple data sources at a processing engine, wherein the multiple data records have different formats from each other and from a pre-established internal data format; parsing in near real time by at least one parser each of the multiple data records into multiple constituent parts; translating in near real time by at least one translator each of the multiple data records using their parsed multiple constituent parts into a pre-established internal data format; comparing in near real time by the processing engine each of the multiple translated internal data records with at least a first enrichment rule to determine if the at least a first enrichment rule is applicable to the translated internal data record; if applicable, enriching in near real time by the processing engine the translated internal data record with additional data pursuant to the at least a first enrichment rule to form an enriched translated internal data record; and transmitting in near real time the enriched translated internal data record to at least one data sink for storage therein, wherein the enriched translated internal data record is available for use by multiple applications.

In a second exemplary embodiment, a process for data collection and conditioning is described. The process includes: receiving multiple data records from multiple data sources at a processing engine; holding the received multiple data records in a first queue to await processing; pulling the received multiple data records off of the first queue by a designated number of ingest nodes for processing; monitoring continuously during the process at least one of first queue size and a rate at which received multiple data records are pulled off of the first queue; determining that the first queue size or rate are outside of an acceptable range; allocating or deallocating ingest nodes to or from the designated number of ingest nodes automatically during the process in accordance with the determination; transmitting from the designated number of ingest nodes in near real time the processed multiple data records to a second queue; holding the received processed multiple data records in the second queue; pulling the received processing multiple data records off of the second queue by a designated number of data sink nodes for processing; monitoring continuously during the process at least one of second queue size and a rate at which received processed multiple data records are pulled off of the second queue; determining that the second queue size or rate are outside of an acceptable range; allocating or deallocating data sink nodes to or from the designated number of data sink nodes automatically during the process in accordance with the determination; and transmitting in near real time each of the processed multiple data records to at least one of the multiple data sinks for storage therein, wherein the processed multiple data record are available for use by multiple applications.

In a third exemplary embodiment, a system for data collection and conditioning is described. The system includes: multiple data transports for receiving multiple data records from multiple data sources and delivering to a first queue for processing, wherein the multiple data records have different formats from each other and from a pre-established internal data format; multiple ingest nodes for accessing the multiple data records and facilitating: parsing in near real time by at least one parser each of the multiple data records into multiple constituent parts; translating in near real time by at least one translator each of the multiple data records using their parsed multiple constituent parts into a pre-established internal data format; comparing in near real time by a processing engine each of the multiple translated internal data records with at least a first enrichment rule to determine if the at least a first enrichment rule is applicable to the translated internal data record; if applicable, enriching in near real time by the processing engine the translated internal data record with additional data pursuant to the at least a first enrichment rule to form an enriched translated internal data record; a second queue for receiving translated and enriched internal data records from the multiple ingest nodes; and multiple data sink nodes for accessing the translated and enriched internal data records and transmitting in near real time each of the translated and enriched internal data records to at least one data sink for storage therein, wherein the translated and enriched internal data records are available for use by multiple applications.

BRIEF DESCRIPTION OF THE FIGURES

The following figures are intended to be part of the disclosure of the embodiments and reviewed in combination with the detailed description provided below.

DETAILED DESCRIPTION

Figure 1:
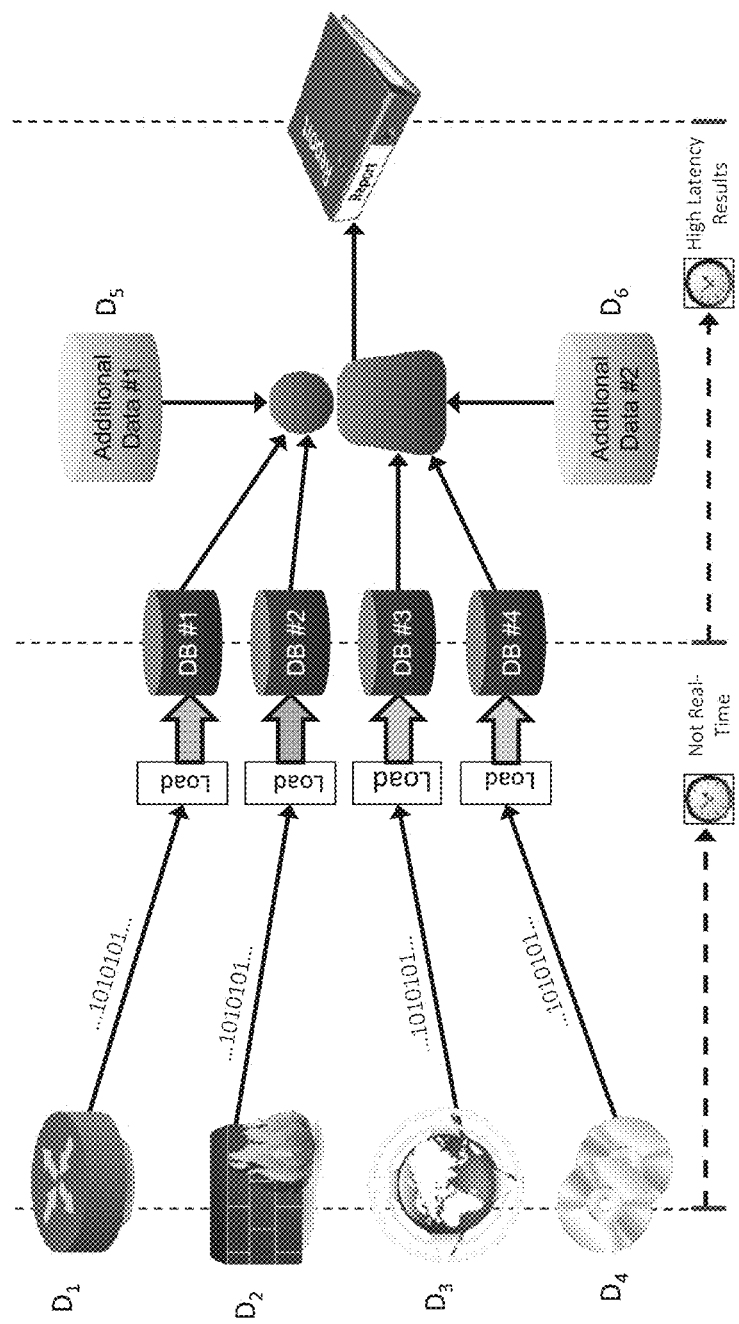
FIG. 1 is a schematic of a prior art system for intake and processing of big data.
Figure 2:
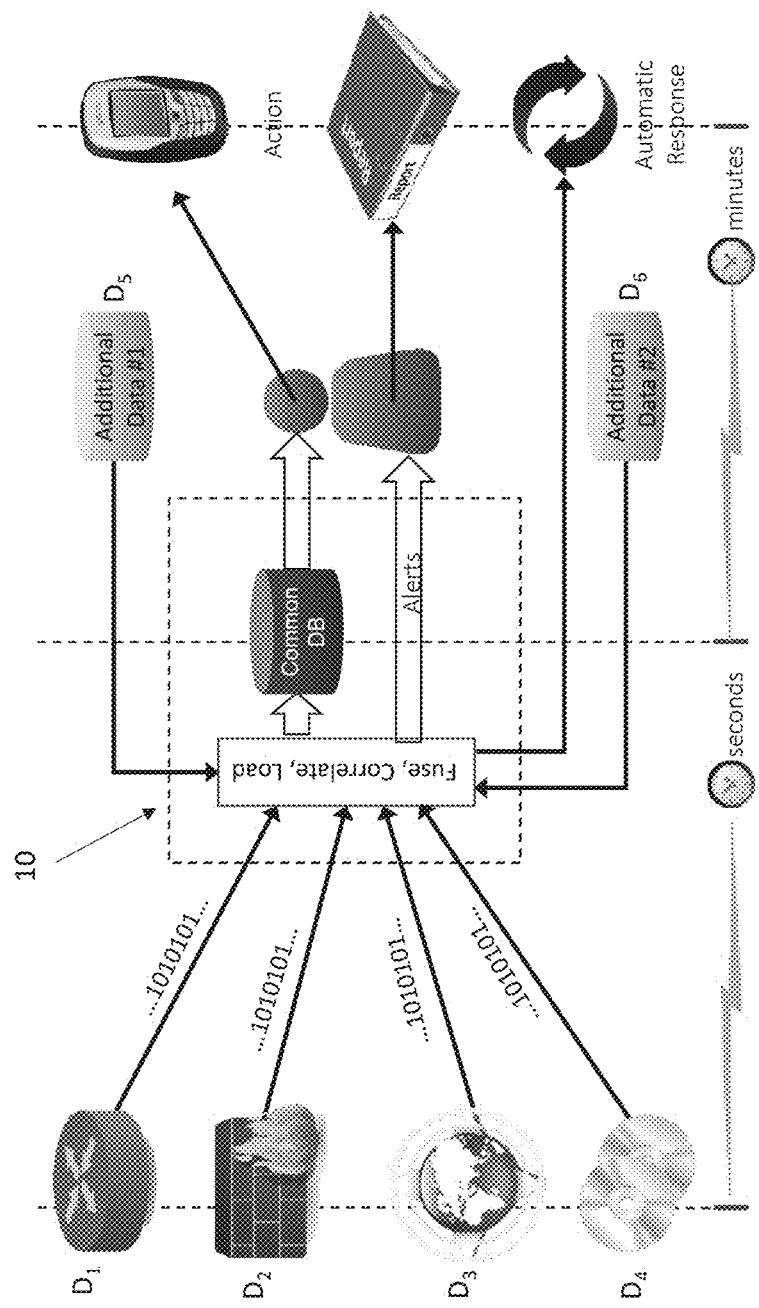
FIG. 2 is a schematic of a system for intake and processing of big data in accordance with an embodiment described herein.

Referring to FIG. 2, the present embodiments include a platform 10 that integrates ETL (extract, transform, and load), real time stream processing, "big data" data sources, i.e., $D_1$ to $D_4$, and enrichment data sources, i.e. $D_5$ and $D_6$, into a high performance analytic system that runs in a public or private cloud. The platform 10 supports sharing of components and plug-ins.

As described herein, real time means responding to the incoming high velocity streaming and likely disparate data within seconds. As such, the platform 10 is provisioned for peak load, as compared to average daily load. Since peak load is often several times the average, and spikes occasionally occur that are hard to predict, when running in a virtualized environment, the present embodiments are designed to scale to meet virtually any load, and can do so automatically. More particularly, running in a public or private cloud computing environment, platform 10 dynamically provisions compute, storage, and network resources to run the system that has been configured. There are two aspects to this. First is simplifying the process of running a system itself. In a traditional environment, you must decide physically where everything runs, which server, what storage, etc., and be sure to set things up that way. However, when running in a cloud environment, platform 10 automatically starts virtual machines, allocates and attaches virtual storage, and establishes the network parameters so the system operates correctly.

The automated scaling is responsive to a platform configuration that monitors processing load, and adds or removes resources as load changes. For example, the platform can be configured such that it maintains the throughput rate required to maintain the data flow rate sent by input sources. The platform can also be configured to add storage when required. This means that if load spikes occur, the system can respond without human intervention.

Figure 3:
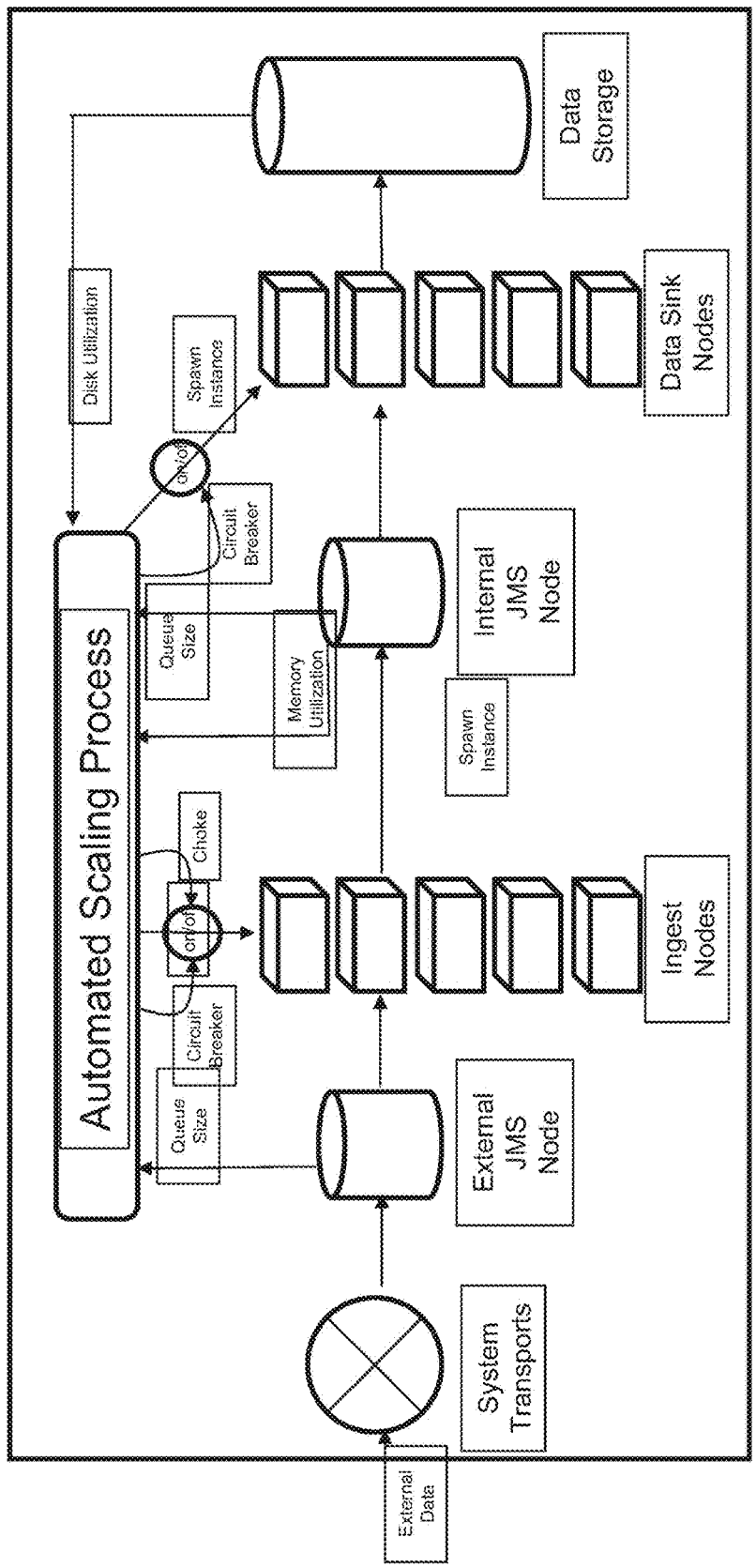
FIG. 3 is a schematic of the automated scaling process in accordance with an embodiment described herein.

Referring to FIG. 3, the mechanism for automated scaling relies upon the monitoring of key processes involving the system JMS messaging and disk usage for the data sinks (described below in detail). As shown, the system transport processes accept external data in native format and convert the data into JMS messages for the external JMS instance to receive and add to the message queue. The ingest nodes then pull messages off the queue for processing. If a condition occurs such that the allocated ingest nodes cannot work the messages off the queue at a sufficient rate, the queue size increases. When this happens, the platform automatically starts additional ingest nodes to provide additional capability to keep up with the pace of the incoming data. Eventually, the ingest processors stabilize relative to the throughput of incoming data, and the messages in the JMS queue are decrease as the extra ingest nodes work them off. In a similar fashion, if the allocated ingest nodes sufficiently process the incoming messages traffic, the system will deallocate ingest nodes, reducing down to a sufficient quantity. The process represents a continual feedback loop that adds or subtracts system ingest instances as required. The trigger point for adding additional nodes is user configurable, allowing for optimization and tuning of the ingest flow process for each particular configures platform.

A similar mechanism also exists for the internal JMS node. Referring to FIG. 3, the ingest processors output enriched data records to the internal JMS node, from which the allocated system data sinks can read and act upon (typically storing) the data records within the messages. The automated scaling monitoring process observes the messaging throughput of the internal JMS node to see if the consuming data sinks are sufficient to maintain pace with the output from the collective ingest nodes. As with the case described for the external JMS node, the automated scaling process spawns additional data sink nodes if needed to maintain pace with message traffic. An additional factor within the automated scaling of data sink nodes is disk space utilization. Several of the platform data sink components persist the data in storage; therefore, the available disk space imposes a limit to the number of additional storage-based data sink nodes that may be added.

Another important feature of the automated scaling process is protection of the system from oversubscribing of resources. Two distinct features fall within this area of system protection. The first is a choke of ingest node allocation. In the event that the internal JMS node memory utilization exceeds a user-defined capacity, the system will invoke a choke mechanism in which allocation of new ingest nodes will be suspended. This has the effect of limiting the rate at which new messages will be added to the internal JMS queue. Note that autoscaling of the data sink node continues, and in fact, should eventually clear the condition. While the choke is engaged, data may begin to back up into the external JMS system, causing its input queue to grow. At some point, the external JMS system invokes its flow control mechanism, which blocks the transport from adding additional data. Ideally, the system would be allocated enough processing resources such that the choke condition would be unnecessary, but it does exist to maintain the running state of the system. The configuration for removing the choke is also user configurable and based upon the internal JMS node memory utilization. It will typically be set below the choke activation point to prevent the choke feature to continually toggle on and off.

The other protection feature of the system addresses conditions that trigger the adding of additional ingest or data sink instances but for which no improvement gains are achieved by the system. This would occur, for example, if resources outside the visibility of the system, such as the network, became a bottleneck. In those cases, adding more processing capability will not alleviate the problem, and in fact, would exacerbate the problem. This is because these new nodes would attempt to consume resources that are already at capacity. The automated scaling method in the system measures response to messaging throughput as it adds new instances as part of the feedback control loop. When the condition occurs where new instances do not increase system throughput, the automated scaling mechanism stops adding resources (however, resources can be removed) for a user defined period of time. This system "circuit breaker" prevents a runaway condition of constantly adding new resources to no avail.

The platform uses shared, reusable components. There are two types of components: plug-ins and data components. Plug-ins are written in Java and add functionality to the platform. There are three types of plug-ins, as follows: parsers which convert a specific data format into name/value pairs (exemplary formats include CSV, XML, JSON, JPEG, etc.); enrichment, which add context to the raw data from input data streams (for example, there is an enrichment that correlates dimension records to the input stream though a simple key-matching strategy); and data sinks which consume the final, enriched record for some purpose (generally speaking, this usually means storing or indexing the data, but a data sink can perform other functions, such as alert filtering).

Data components include data models and dimension data. Currently, data components and plug-ins are public or private. A public component is available to all and can be reused. A private component only applies to the current tenant. The platform facilitates and allows for the development of a set of data components for a particular purpose or vertical market and sharing of components among peers. For example, a set of standard data components can be developed specifically for cyber security threats. This standard set can then be extended to add additional functionality.

Figure 4:
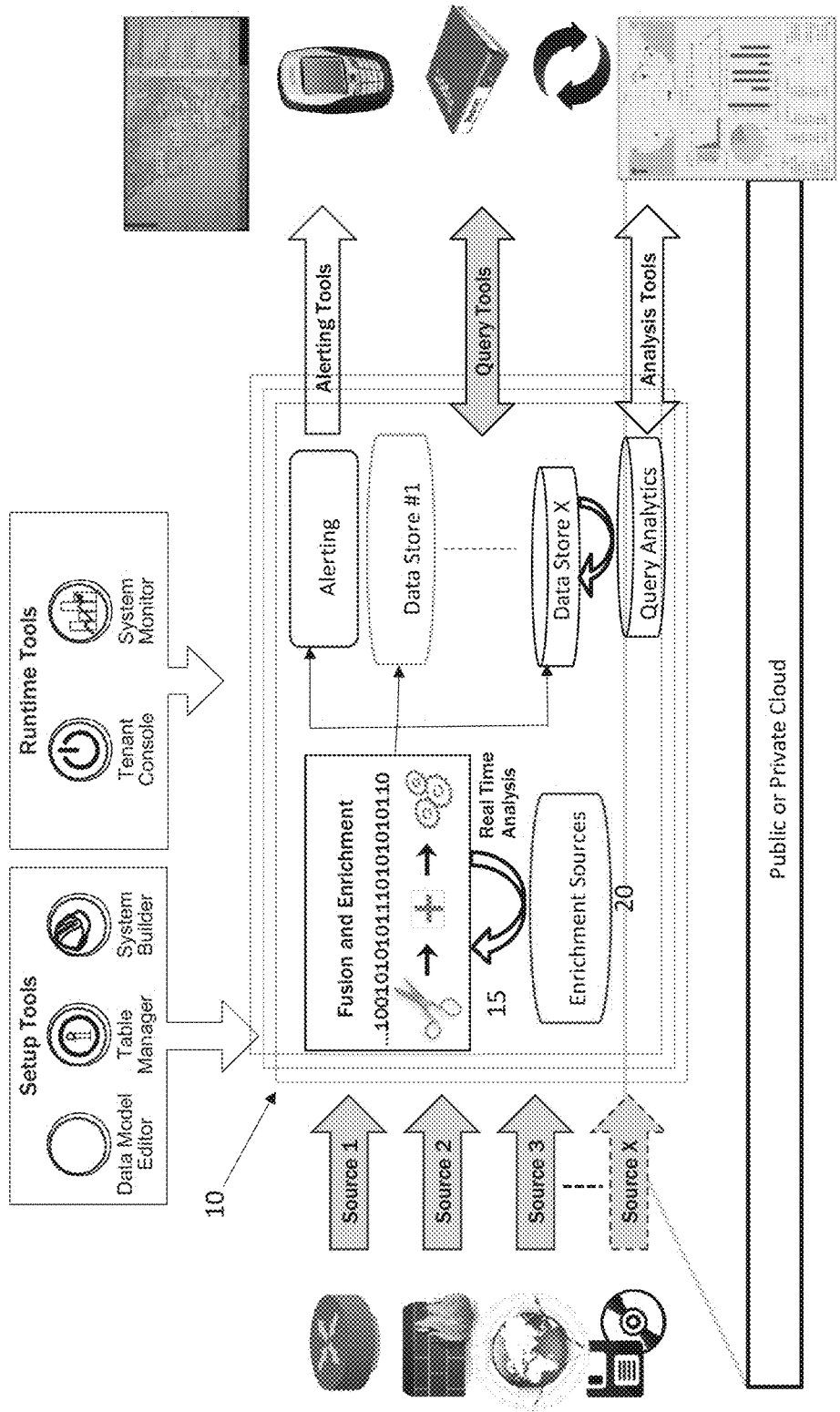
FIG. 4 is a more detailed schematic of a system for intake and processing of big data in accordance with an embodiment described herein.

In order to achieve a rapid response and situational awareness from real time alerts, they need to be understandable and actionable. This would not be the case if, for example, the data feed is full of codes or magic numbers, or if critical pieces of information were missing but available from another data source. Accordingly, referring to FIG. 4, the platform 10 includes a correlation and enrichment engine 15 (hereafter "processing engine") which adds context and meaning so that real time alerts are meaningful. This makes the alert understandable and actionable.

Data correlation is achieved by taking diverse data feeds (e.g., $D_1$ to $D_4$) and normalizing them to a common data model. However, data models in a SQL database are very rigid in that only one data model can be in force at any given moment, and changing them requires data migrations and other fixes that limit "data agility." But there is still value in having a common model upon which application and algorithms can rely. For example, if you have a dozen algorithms and applications that depend on a common data model, if you add a new data source, none of those algorithms and applications needs to change. Platform 10 takes a unique approach to addressing this issue by allowing data models to change more easily. To accomplish this, data models are dynamic and versioned, and a new or updated model can be deployed quickly as needs arise. No data migrations are necessary, because the system allows different versions of the same data model to exist in the data store at the same time. The new data model is deployed and it takes effect. Each record is tagged with its data model and version if needed.

Enrichment is the process of adding meaningful information to data feed records before they are stored or alerted upon. This is similar to the idea of dimensions in dimensional modeling. In dimensional modeling, a "dimension" is often a separate data source that is correlated with the input feed. By way of example, think of a point of sales (POS) transactions and a customer database. Each sale is correlated with a customer record in a customer dimension table. This adds additional information to the sale about that customer to the POS data record.

To effectively use the "NoSQL" databases to support big data, in certain embodiments, the platform 10 "pre-joins" the input feed to dimensions at ingest time. Continuing the POS example above, this means that all the fields from the customer record from the customer table, that matches the customer referenced in the sale, is merged with the sales record. Now when the record is queried, no joins are required—the data is already in the record. Pre-joining is just an example of a way to add meaning and context to the data. Generally, any algorithm that runs on the data and adds something to it is "enrichment." Data that comes from dimension tables is one kind of enrichment. Others include, for example, an algorithm that takes an IP address and figures out the CIDR network it is part of, or examines an email feed to see if it is a phishing attack, or an algorithm that converts a latitude/longitude pair to a grid reference. The dimension tables and algorithms that add to the data are generally referred to as enrichment sources 20. After correlation and enrichment, a single comprehensive and fully expanded record exists for use in alerting, querying, analysis and other applications within seconds.

Figure 5:
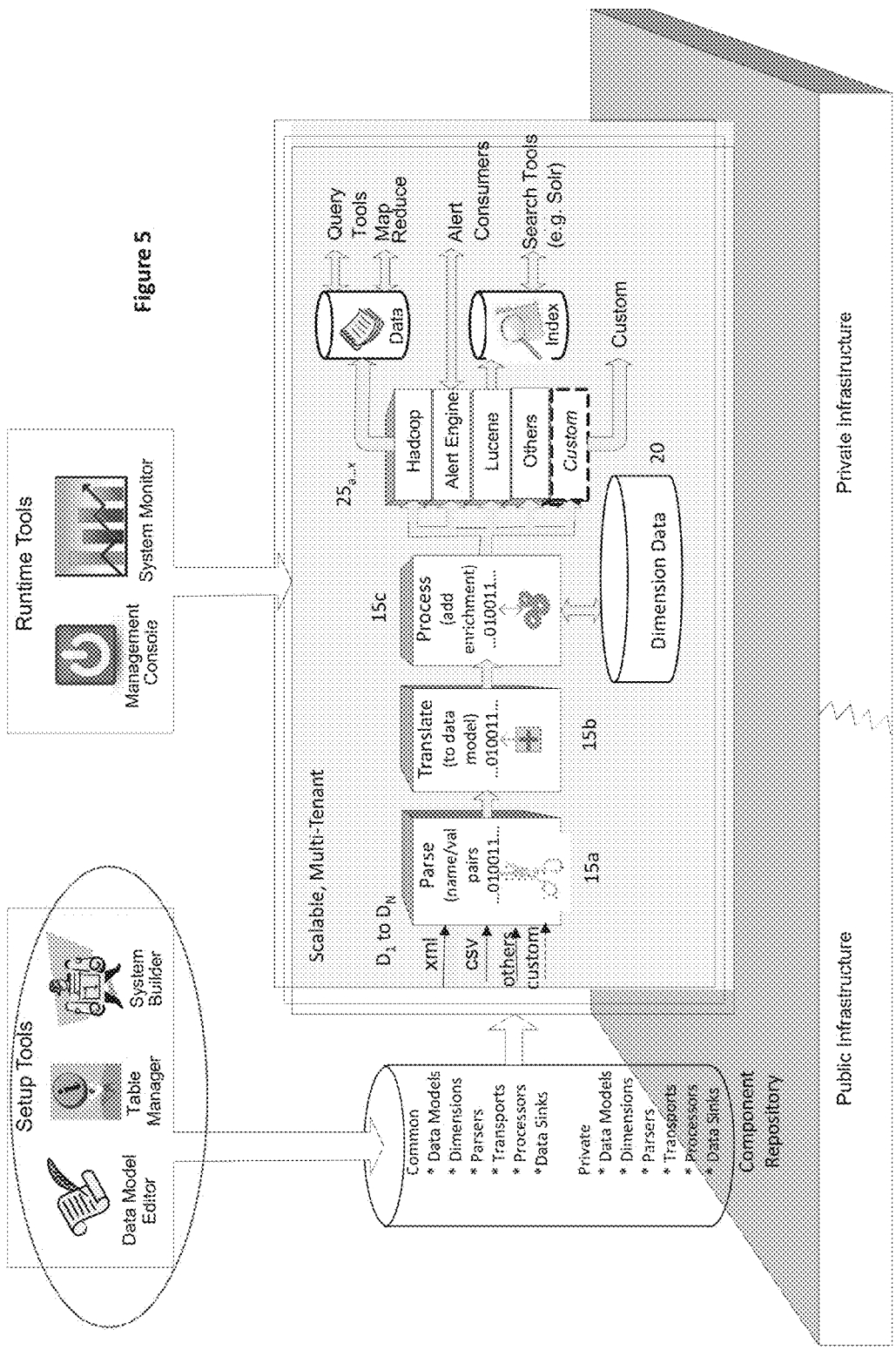
FIG. 5 is a still more detailed schematic of a system for intake and processing of big data in accordance with an embodiment described herein.

The processes and functionality discussed above are discussed below in detail with reference to FIG. 5, along with description of configuration specifications. The functionality and implementing components and subcomponents, i.e., software and/or hardware, are singularly referenced in the figures, but one skilled in the art recognizes that such components and subcomponents may be implemented through recognized processing software, hardware or a combination thereof. Further, the various components and subcomponents need not necessarily be co-located in a single location, or, in some instances, be under the direct control of the same entity. Further still, it is recognized that certain of the various components and subcomponents may be located on a public infrastructure, while others may be located on a private infrastructure. Some or all of the configurations of the processing pipeline described below may be performed by a user through, for example, a series of web-based application programming interfaces (APIs).

Data Model

A data model is the foundation for defining and managing data in accordance with the embodiments described herein. The data model defines the input sources, the internal normalized data model (or format) that the embodiments use to organize data, the parsing techniques used to translate incoming data into the internal format, and the sources and types of dimensional data that will be used to enrich, i.e., enhance or further describe, the data (e.g., replacing a ProductiD with a ProductName from a supporting relational table), and any additional algorithmic processing on the data resulting in appending the computed results to the data. The data model specifies three components: Input model, which is a JSON-based model that specifies how the data will look when it enters the system and is mapped into a normalized model, this is the data model for the internal format; data sources which are specifications for parsing 15a the incoming data and mapping/translating 15b each field to the input model; and enrichment processing 15c which are rules for enhancing the data with dimensional data 20 for additional context and meaning.

The input model is defined to include: a name for the input model; a name for each field in the input model; the data type of each field, e.g., String, Number, Date/Time, Object, and Array. The input model includes fields that are common to all data sources, and it may also include fields that are specific to just one or more data sources. Common fields provide a data provenance mechanism to embed the data information source to the data record. This can be important for applications requiring auditing of data and forensic analysis. Similarly, common fields include a data labeling mechanism that can assign data classifications. This feature can be used to restrict access to data records to only individuals or groups having permission to access data based upon its label.

Data sources $D_1$ to $D_N$ can originate from virtually any data store or format: a data stream feeding, real-time transactional records, multiple relational databases, web sites, RSS feeds, SIEM files, email archives, etc. The primary data feeds will contain the fact records that are central to the input model. Configured input data sources include name and location of each incoming data source that will provide data. Additionally, file format, and the parser type 15a required to extract data fields for input are defined, for example:

Binary: a user-configurable parser that is used to extract fixed fields from byte strings in binary files;

CEF: a parser that uses the Common Event Format from ArcSight®, an open standard for logging security-related information in a common event log format;

CSV: a commonly used parser to extract comma-separated values from plain text files; this parser is user-configurable;

Email: a parser that works with the RFC 822 ARPA email text format (which specifies the structure of email messages, including attachments, to and from fields, etc.);

EXIF: a configurable parser that works with the Exchangeable Image File format used for handling image and sound files from digital cameras;

JSON: a configurable parser that extracts data from text formatted in the JavaScript Open Notation standard;

Libpcap: a parser that works with packet captures in the UNIX Libpcap library;

XML: a configurable parser that extracts data from the Extensible Markup Language format.

A Field delimiter type is defined and includes: Comma, Pipe or New line. For each incoming data field, the original source specifications for the parser are required and include: Field name; Field data type (String, Number, Date/Time, Object, Array); Translation rules for mapping a field into the input model (JSON representation, Conversion requirements (date conversions), Constant value, Processing rules (could be specified in a script that you run on the data source); If a field should be enhanced with data from another table or source, identify the dimension table name and column(s) that will provide the enrichment data; and Input date format.

Data Transport

Each data source must be associated with a transport mode. Ingest supports several secure automated transport mechanisms, including file-based transfer protocols, streaming TCP and UDP connections, external database queries, and unstructured documents. For example, the TCP transport establishes a TCP socket listening to a port, converts it to JMS messages, and pushes the data into the JMS external node. Each parser can be assigned to a different transport type. Exemplary transports include polling services. One exemplary service watches local file system. Another exemplary service retrieves data from a database and pulls it into the platform by running an SQL select query against any database. The database can be queried regularly, starting at the point where the query last left off. An S3 bucket is used to store a backup copy of the data file. Yet another service copies data directly from a JMS server to the platform server without a transport. The JMS Bridge Service pushes data directly onto a JMS queue without a transport. For example, there could be two JMS servers in play: a corporate JMS server and the platform JMS server; the bridge pushes data from enterprise queue to platform.

For static files, such as legacy data, the S3 transport service may be used. The S3 transport can be configured two ways: as a one shot event, it pulls data from an Amazon's S3™ (Simple Storage Service™) file and pushes it to the platform JMS queue or it can be configured to poll an S3™ bucket regularly at a set time interval. Additional transport services can be used to read data in a TCP stream, wherein the TCP socket listens to a port, converts the data to a JMS message, and puts it on the JMS external queue. There is also a transport service that captures network packets in a UDP stream, converts the data to JMS messages, and sends them to the JMS external node. Finally, transport service is available to read the contents of a URL and put it on the JMS input queue. This transport may be used to pull data from an RSS feed or from any service that pulls resources from another organization or data source.

Data Enrichment

As discussed briefly above, the platform performs various data enrichment functions during front end data processing 15c. For example, dimensional enrichment associates a secondary data table with a primary data source, to add data to each record that better describes a data element. For example, returning to the previous from a POS example, POS transaction stream data records could be enhanced with the product names (replacing product IDs), customer names (to replace customer IDs), mailing addresses, etc. The enhancement data comes from dimension data tables specified by the end user as part of the configuration of the platform data model discussed above. For each dimension table, end users identify the fields in the input model that will be enhanced with the dimensional data. Additionally, the platform may also implement generalized or algorithmic enrichments that do not require dimension tables as the source for enhancement data. Generalized enrichments use data from proprietary or public sources. For example, to add the geographic location of an airport, the platform converts standard 3-letter airport codes to latitude/longitude coordinates.

By way of example, for dimension table specifications, end users inventory each enrichment source (dimension table) for its content, format, and structure. It should be noted how each enrichment source correlates to the main data feed in order to specify translation rules for the data fusion engine. The following information is used to configure each dimension table: Name of dimension table, Primary key, Column/Field name to extract, Data type (i.e., Varchar, Decimal, Date) and if Nulls are allowed in the field.

Dimensional enrichments require the specification of dimension tables, which store the enhancement data that a user wants to add to native input data in the platform input model. Users can define a dimension table at any time, but it is most logical to define the tables before specifying enrichments. In other words, when possible, users should define source data, including dimension tables, before configuring data use within the platform. Defined data tables populate the dimension table enrichments specified by the user. There are three types of keys considered. Every data table has a master key which aids in read/write performance and with data integrity. This is the primary key. The primary key defines one or more columns which uniquely identify a row within a table. The primary key can be either a natural or a surrogate key, with industry best practices dictating that the primary key would be a surrogate key. Most database systems only allow a single key in a table, the primary key. However, you can have uniqueness indexes which identify secondary keys, which can either be natural or surrogate keys.

A natural key defines one or more columns that uniquely identify each row in the table. The columns used in a natural key must be part of the original data set. For example, a unique customer key may be built with the C_NAME and the C_SSN columns. Or a table of airport codes may only need one field—the 3-letter airport code—as a natural key that is unique for each record. Natural keys are most often defined with two or more columns. This key is used to index the records in the dimension table and to search the table for a matching row. Indexes are used when the enrichment engine has to do a full look-up on the dimension records.

A surrogate key is a single column added to the original data set, to uniquely identify each record. Any column type (string, number, alpha-numeric) can be used as a surrogate key as long as it is unique. However, a sequential numeric column is usually used for performance and simplicity. A surrogate key is required to insert a record into the platform. An exception to this requirement is made if a user sets an enrichment cache to ignore an unknown record (and not add it to the database (see below)).

There are no default dimension tables or pre-defined enrichment tables. A dimension table may originate from an SQL table, located in a corporate data warehouse. It may be a simple CSV file linked to other systems. Or it may be an XML file in a custom application. Once the dimension tables are defined, the source enrichment data is imported therein via, e.g., a CSV file or a ZIP file.

Once columns have been specified for a dimension table, and indexes and keys have been defined for the records, the dimension fields can be mapped to the input model fields that will be enriched with data from the particular dimension table. Pre-assigned enrichment field names are referenced when dimension table enrichment models are specified. Working with one field at a time, dimension table columns are mapped to input model fields using assigned enrichment roles. The assigned enrichment roles indicate if a dimensional column is used to enrich input records, or if it is a key for enrichment look-ups. Prior to mapping, a role is chosen for each column in the dimension table. Values in the surrogate key dimensional column are unique sequential numbers used to insert a record into the platform and need to be defined if the enrichment cache is set to Add Record to DB. The natural key dimensional column represent a unique key, indexed for enrichment look-ups. Values in the data dimensional column will be used to enrich input model records, to enhance data sources with additional, clarifying information. Any "not used" dimensional column is ignored for enrichment purposes. Enrichment field details map dimension data columns to enrichment fields in the input model. This is where the enrichment field names that are used to enrich the input model are assigned. These field names are stored in JSON in the preferred embodiment.

Now, it would be too slow to do full look-ups to match every transactional record against the dimension records, so the platform uses a configured enrichment cache for faster processing. When configuring the enrichment cache, there are several specifications to be defined. First, the size of the cache is defined by specifying how many dimensional records should be held in memory for matching against input records (default=15,000 rows). This number will depend on the size of each dimension table. Additionally, it must be determined which resources are available on the ingest node for dedication to the enrichment cache. There is a trade-off between resources and performance that should be tested prior to implementation of the platform. Further, a load strategy is selected for the enrichment cache, to specify how the cache is initialized. Speed of cache startup versus potential cache misses if the cache has not yet reached its maximum size should be considered. Load strategy options include: completely filling the cache as soon as the system starts up the ingest node (for smaller dimension tables); creating the cache only as data comes in, e.g., for dimension records that are used infrequently (for example, customer names for a big-box store, where customers make purchases infrequently); or creating the cache when the system starts up the ingest node, by loading dimension records into the cache in the background or on-demand when a record needs to be processed.

While performance could decrease if look-ups occur too frequently, the cache "learns" as processing continues, keeping the most recently used dimension records in memory and dropping the least frequently matched records out of the cache.

Figure 6:
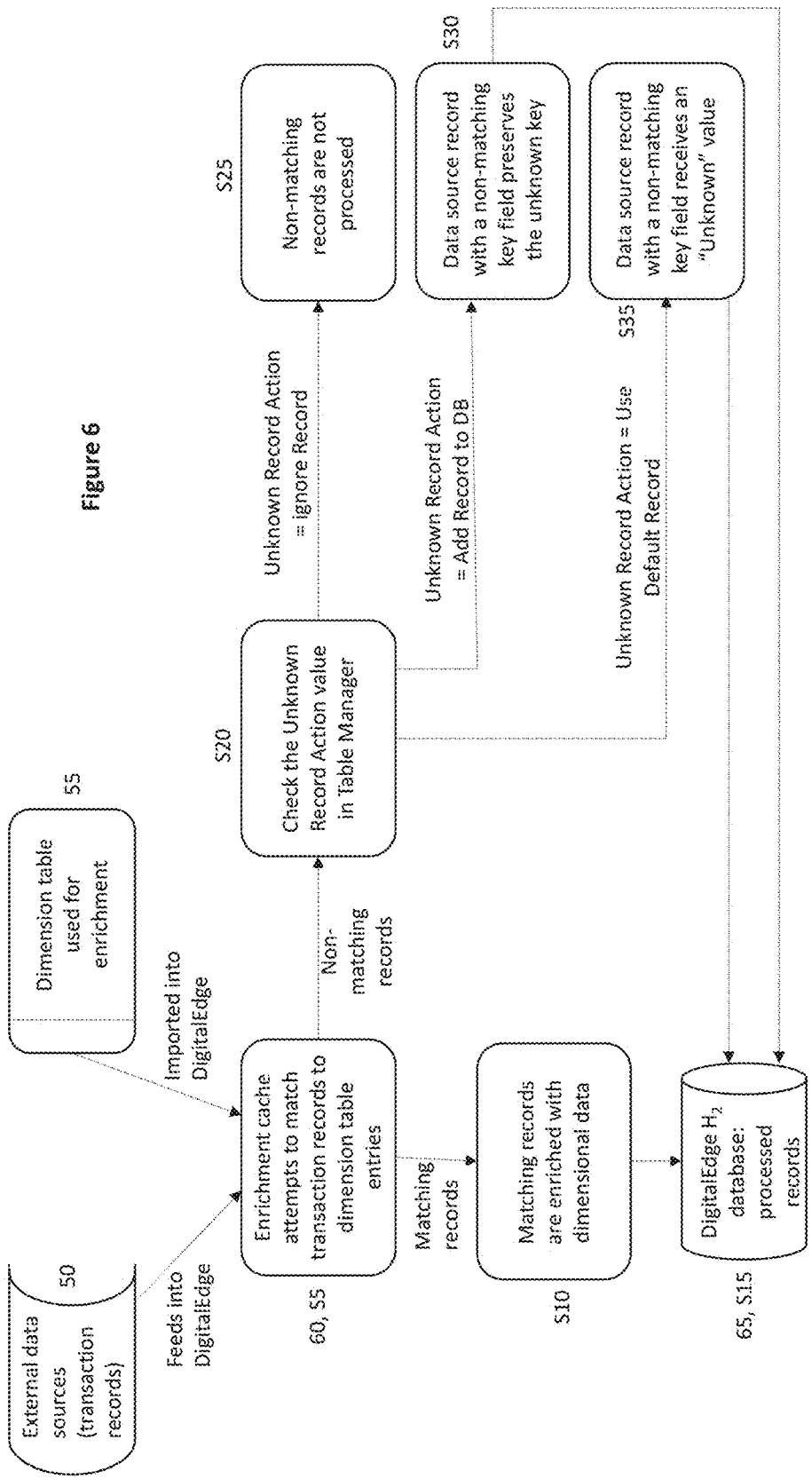
FIG. 6 is a process flow for comparing incoming external data with dimension enrichment tables to determine processing details.

Referring to FIG. 6, once configuration is complete, when the platform ingests data source records 50, the enrichment processor checks input records for matches S5 against the dimension table records 55. The enrichment cache 60 can hold dimension records in memory, but if no match is made between an incoming record and the cache, the enrichment engine does a full look-up on the dimension data, using the user specified indexes for a particular table. When matching records are found as a result of the comparison S5, the transaction records are enriched with dimensional data from the dimension table S10 and the enriched records are stored in one or more platform databases 65, S15.

Alternatively, when the enrichment engine attempts to match input model records with dimension tables S5, the system may occasionally locate an unknown record. For example, a new customer may not be in the CUSTOMER database yet, so when a transaction comes in with a newly created CUSTOMER_ID that does not match a key in the CUSTOMER dimension table, the system will fail to match the record to the CUSTOMER dimension table. When this occurs, the platform needs instructions for handling the unknown record S20. These instructions may include one of the following.

The instructions may be to ignore the record, i.e., stop processing the record entirely S25. The record will not be added to the platform database and the platform will take no further action on the record.

The instructions may be to add the incoming record into the platform database under a new surrogate key S30. The natural key and data values identified in the enrichment configuration will be stored in the table. Using the sales transaction example, a new transaction record is added to the platform database with a CUSTOMER_ID that does not match a record in the CUSTOMER dimension table.

Further still, the instructions may be to look up a default row in the dimension table and use it to enrich the record S35. Using the sales example, if a new customer has not yet been added to a dimension table, the CUSTOMER_ID column in the sales transaction record may not find a match in the CUSTOMER dimension table. In that the platform is instructed to add a value such as "unknown" or "UNK" to the enrichment field of the transaction record and continue processing other records. The output records from S30 or S35 are stored in one or more platform databases 65.

In addition to the dimension table enrichment (described above), the embodiments also support generalized, algorithmic enrichment. Some non-exhaustive examples of generalized, algorithmic enrichment are discussed herein.

Flag local network which determines if a given IP address is local or private. It sets the isPrivate and isLocal tags to yes or no based on that determination.

IP network with creates the classless inter-domain routing (CIDR) formatted IP notation that corresponds to a given IP address.

Math enrichment which runs a mathematical expression that you create against the data. User specifies the formula with the enrichment parameters. For example, user could calculate the time between two date stamps, or the distance between two locations.

Postal location which computes the nearest zip code, city, state, or country from a given latitude/longitude pair.

Record history which adds an array of records that recently passed through the platform and that match a specified field (may use, e.g., MongoDB data sink for storing and matching transaction records).

SQL select enrichment to look up information in an SQL database with a given query.

Yet another enrichment may be anonymization of certain data so that the data may pass securely through the public cloud or other public environment and be reverse anonymized at the secure user. For example, when dealing with personal health information (PHI), the confidentiality of such information is critical. Accordingly, various fields containing PHI could be searched and replaced with tokens and then reversed tokenized once the data reaches the appropriately secure destination.

Further to configuring the enrichment process flow, the destination or output field can be selected to be: the input field, overwritten with enriched data or a newly created field, solely for enrichment data. Further still the enrichment data may be filtered prior to saving. Enrichment data often comes in as multiple fields in an object, assigned to a destination output field. However, there are times when you don't need to save all the enrichment fields, but you just need to keep one column in the output field. For example, when you define a postal_location enrichment, the algorithm converts latitude/longitude data and returns three enriched fields: city, state, and zip code. If you want to filter the enrichment record and exclude state and zip code information, you could filter the enrichment and just save the city field.

Additional System Components and Architecture

To complete configuration of the processing pipeline and system architecture data sinks and user applications are also identified.

Data sinks $25_{a \ldots x}$ are queues, servers, or databases that receive data from the processing engine and store or process data for future use. For example, data stores are used to index data for queries, to store historical data, or to process data for alerts. Selection of data sinks should be determined in accordance with intended use of received data. Some exemplary data sinks are described herein.

External HBase data sink stores data in an existing Hadoop/HBase cluster that is external to and not managed by the platform. For end user organizations already using applications that use HBase, platform processed data can be sent to that cluster with this data sink.

External HDFS data sink stores data in an existing Hadoop cluster that is not managed by platform (compatible with Cloudera CDH3uX releases). For end user organizations already using Hadoop clusters, platform processed data can be sent to that cluster by configuring a communication connection with this data sink.

External Hive data sink is similar to the Hive data sink, but stores data in an existing Hadoop/Hive cluster that is not managed by the platform. For end user organizations already using Hive clusters, platform processed data can be sent to that cluster by configuring a communication connection with this data sink.

HBase data sink stores processed data in an HBase database that is managed internally by the platform. HBase was originally created to handle petabytes of data.

Hive data sink stores processed data in the Hadoop/Hive environment and is managed internally by the platform. Hive was originally created to interface SQL databases with Hadoop, so organizations that were relational-based could continue to work in an SQL-like environment while interfacing to Hadoop MapReduce technology. This data sink is used to create a Hive cluster that is managed by the platform.

Lucene indexing data sink is used if end user organization intends to have data searchable with the Search or SearchAPI web applications. The Lucene data sink uses a copy of the processed platform data and builds an inverted index for real-time and near real-time search.

MongoDB data sink is a general all-purpose data sink that stores processed platform data in a MongoDB® database which is managed by the platform and can scale automatically.

Alerting data sink filters processed records for alert triggers and sends out alert messages either as email messages or as messages in a JMS topic. The data sink does not store processed records. This data sink is used to implement end user data systems that are configured to identify possible cybersecurity breaches, situational anomalies, or potential fraud.

A primary reason for doing complex configuration of a platform data model is to make information available to users in real time for analysis. To that end, the platform provides several user applications as plug-ins (hereafter "Plug-in apps"), or processed platform records can be fed into particular applications of an organization (hereafter "User apps") for additional reporting and analyses. User apps are configured as specific Web Apps in the platform. Web Apps include two types: applications that end users will use to search for and analyze data and REST APIs.

Plug-in apps may include: Alert Controller to manage alert criteria, notifications, and subscriptions; Alerts API to manage alert criteria used to generate notifications of potential threats or fraud; Metrics API to collect statistics on system performance; Search for real time and near real time full text queries; Search API to build a custom search capability for your system.

To feed platform data into a User app, an externally facing data sink such as the Scripting Data Sink or the JMS Data Sink may be configured (see above).

Defining Alert Rules

As referenced above, a particularly useful feature of the platform is the ability to generate real-time alerts (notifications) to users about a potential threat or fraud in progress. The platform can place actionable intelligence in the hands of decision makers within seconds of an anomalous event occurring, not days or even hours after the fact. Alerting aids in the detection of fraud and threats, and facilitates rapid response to an unfolding situation. There are three phases to configuration and implementation of the platform alerting mechanism. Initially, alert criteria are defined to specify business rules to define what a threat would be to the organization. For example, a Systems Administrator may want to know when an individual attempts to access a company intranet from an outside IP address. Or a bank may want to know if an employee is frequently servicing transactions on his own account.

Next, the platform alert engine analyzes data for potential threats by attempting to match the alert criteria filter rules against processed records.

Finally, notifications are sent in real time of a threat in progress. That is, if a match is found between a record and the alert filter, a notification can be generated and sent to one or more email addresses, as text messages, to the console, or on a JMS queue.

Exemplary scenarios where one or more of the combinations of functionality of the platform described herein may be particularly useful are described below.

The platform may help prevent check fraud. Financial services firms face explosive growth in cyber attacks and bank fraud. For example, a large financial institution wants to detect scenarios in which a check cashing transaction occurs in one account at two separate branches simultaneously or in close sequence. This so-called "branch hopping" can indicate potential fraud. In this case, the platform provides increased threat awareness by detecting fraud as it occurs and mitigating it through a combination of hardware, software, and services. The platform provides an immediate return on investment by detecting fraud as it occurs rather than after the fact and attempting to retrieve stolen funds.

The platform may be particularly useful in the healthcare industry. The platform can collect volumes of patient information, which is controlled by compliance regulations. The platform can be used for rapid diagnoses when there is a limited amount of time.

The platform may be particularly useful in the telecommunications industry. The platform can protect against customer identity data, guard against security hacks, and analyze geospatial data for suspicious activity. For example, the platform may be used to perform deep analytics of DNS communications to identify complex attack trends and store historical archives of DNS transactions. The system can deliver capabilities such as: enrich data flow pipeline, store data for archive and a basis for distributed queries, process data through analytics algorithms and visualize threat vectors for broader posture of the DNS defense environment.

The platform may be particularly useful in the transportation industry. The platform can take advantage of the geospatial analytics to track vehicles and packages, to analyze patterns in pathways and to flag abnormal behavioral states.

The platform may be particularly useful in mining and analyzing for privacy breaches and insightful business intelligence.

The platform may be particularly useful in e-commerce applications to safeguard customer records and protect against credit card fraud and hackers.

One skilled in the art recognizes that the examples provided in the present disclosure are not limited as such. There are numerous variations to components and functionality described as part of the overall architecture and processes of the platform that are known and would readily be considered to be within the scope of the invention.

The invention claimed is:

1. A process for data collection and conditioning comprising:
   receiving multiple data records from multiple data sources at a processing engine;
   processing each of the multiple data records from each of their respective native formats into an identical internal format;
   holding the received and formatted multiple data records in a first queue to await processing;
   pulling the formatted multiple data records off of the first queue by a designated number of ingest nodes for processing;
   monitoring continuously during the process at least one of first queue size and a rate at which formatted multiple data records are pulled off of the first queue;
   determining that one or both of the first queue size or rate of receipt are outside of a first acceptable range;
   allocating or deallocating ingest nodes to or from the designated number of ingest nodes automatically during the process in accordance with the determination;
   transmitting from the designated number of ingest nodes in near real time the formatted multiple data records to a second queue;
   holding the received formatted multiple data records in the second queue;
   pulling the received formatted multiple data records off of the second queue by a designated number of data sink nodes for storage;
   monitoring continuously during the process at least one of second queue size and a rate at which received formatted multiple data records are pulled off of the second queue;
   determining that one or both of the second queue size or rate of receipt are outside of a second acceptable range;

allocating or deallocating data sink nodes to or from the designated number of data sink nodes automatically during the process in accordance with the determination; and transmitting in near real time each of the formatted multiple data records to at least one of the multiple data sinks for storage therein, wherein the formatted multiple data records are available for use by multiple applications.

2. The process of claim 1, further comprising automatically stopping allocating of ingest nodes when the second queue size reaches a predetermined limit.

3. The process of claim 1, further comprising:
monitoring continuously a response to allocation of one of ingest nodes and data sink nodes to determine if processing throughput is improved thereby; and
stopping allocation if it is determined that processing throughput is not improved.

4. The process of claim 1, wherein the first and second queue are Java Messaging Service (JMS) queues and the internal format is a JMS format.

5. The process of claim 1, further comprising:
comparing in near real time by the processing engine each of the formatted multiple data records from the ingest nodes with at least a first enrichment rule to determine if the at least a first enrichment rule is applicable to at least one data element in one or more of the formatted multiple data records; and
if applicable, enriching in near real time by the processing engine the at least one data element in one or more formatted multiple data records with additional data pursuant to the at least a first enrichment rule to form one or more enriched formatted data records.

6. The process of claim 1, wherein processing each of the multiple data records from each of their respective native formats into an identical internal format further comprises:
parsing in near real time by at least one parser each of the multiple data records into multiple constituent parts; and
translating in near real time by at least one translator each of the multiple data records using their parsed multiple constituent parts into the identical internal format.

7. The process of claim 1, wherein the identical internal format includes multiple fields, wherein at least a first of the multiple fields is common to all of the multiple data records from the multiple data sources and at least a second of the multiple fields is unique an individual class of the multiple data records.

8. The process of claim 1, wherein the multiple data sources include at least two sources selected from the group consisting of a relational database, a website, an RSS feed, a SIEM file, an e-mail archive.

9. The process of claim 6, wherein the at least one parser is selected from the group consisting of a comma-separate value parser, an e-mail parser, an exchangeable image file format (EXIF) parser, a JavaScript Open Notation (JSON) parser, a Libcap parser and an XML parser in accordance with one or more native formats of the multiple data records.

10. The process of claim 5, wherein the at least a first enrichment rule is selected from the group consisting of an algorithmic enrichment rule and a dimensional enrichment rule.

11. The process of claim 10, wherein the algorithmic enrichment rule is addition of geographic location.

12. The process of claim 10, wherein the dimensional enrichment includes:

comparing data elements from each of the formatted multiple data records with secondary data in a data enrichment table; and
modifying the data elements in accordance with the secondary data.

13. A process for data collection and conditioning comprising:
receiving multiple data records at varying receipt rates from multiple data sources at a processing engine;
processing each of the multiple data records from each of their respective native formats into an identical internal format, wherein processing includes,
parsing in near real time by at least one parser each of the multiple data records into multiple constituent parts; and
translating in near real time by at least one translator each of the multiple data records using their parsed multiple constituent parts into the identical internal format;
holding the received and formatted multiple data records in a first queue to await processing;
pulling the formatted multiple data records off of the first queue by a designated number of ingest nodes for processing;
monitoring continuously during the process at least one of first queue size and a rate at which formatted multiple data records are pulled off of the first queue;
determining that one or both of the first queue size or rate of receipt are outside of a first acceptable range; and
allocating or deallocating ingest nodes to or from the designated number of ingest nodes automatically during the process in accordance with the determination to maintain a receipt rate that is approximately equal to a highest of the varying receipt rates.

14. The process of claim 13, wherein processing each of the multiple data records from each of their respective native formats into an identical internal format further comprises:
parsing in near real time by at least one parser each of the multiple data records into multiple constituent parts; and
translating in near real time by at least one translator each of the multiple data records using their parsed multiple constituent parts into the identical internal format.

15. The process of claim 13, wherein the identical internal format includes multiple fields, wherein at least a first of the multiple fields is common to all of the multiple data records from the multiple data sources and at least a second of the multiple fields is unique an individual class of the multiple data records.

16. The process of claim 13, wherein the multiple data sources include at least two sources selected from the group consisting of a relational database, a website, an RSS feed, a SIEM file, an e-mail archive.

17. The process of claim 14, wherein the at least one parser is selected from the group consisting of a comma-separate value parser, an e-mail parser, an exchangeable image file format (EXIF) parser, a JavaScript Open Notation (JSON) parser, a Libcap parser and an XML parser in accordance with one or more native formats of the multiple data records.

18. The process of claim 13, further comprising:
comparing in near real time by the processing engine each of the formatted multiple data records from the ingest nodes with at least a first enrichment rule to determine if the at least a first enrichment rule is applicable to at least one data element in one or more of the formatted multiple data records; and if applicable, enriching in near real time by the processing engine the at least one data element in one or more formatted multiple data records with additional data pursuant to the at least a first enrichment rule to form one or more enriched formatted data records.

19. The process of claim 18, wherein the at least a first enrichment rule is selected from the group consisting of an algorithmic enrichment rule and a dimensional enrichment rule.

20. The process of claim 19, wherein the algorithmic enrichment rule is addition of geographic location.

21. The process of claim 19, wherein the dimensional enrichment includes:
   comparing data elements from each of the formatted multiple data records with secondary data in a data enrichment table; and
   modifying the data elements in accordance with the secondary data.

* * * * *